United States Patent [19]

Ehrenfreund

[11] 4,348,412

[45] Sep. 7, 1982

[54] INSECTICIDAL PHENYLUREAS AND METHODS OF USE THEREOF

[75] Inventor: Josef Ehrenfreund, Allschwil, Switzerland

[73] Assignee: Ciba-Geigy Corporation, Ardsley, N.Y.

[21] Appl. No.: 166,634

[22] Filed: Jul. 7, 1980

[30] Foreign Application Priority Data

Jul. 11, 1979 [CH] Switzerland ............... 6475/79
Nov. 22, 1979 [CH] Switzerland ............. 10417/79
Jun. 3, 1980 [CH] Switzerland ............... 4286/80

[51] Int. Cl.³ ............... A01N 47/28; C07C 127/22
[52] U.S. Cl. ............................. 424/322; 564/44
[58] Field of Search ..................... 424/322; 564/44

[56] References Cited

U.S. PATENT DOCUMENTS 3,989,842 11/1976 Wellinga et al. ............ 424/322
4,085,226 4/1978 Sirrenberg et al. .......... 424/322
4,089,975 5/1978 Wade et al. ................. 424/322
4,139,636 2/1979 Sirrenberg et al. .......... 424/322
4,170,657 10/1979 Rigterink .................... 424/322
4,277,499 7/1981 Sirrenberg et al. .......... 424/322

FOREIGN PATENT DOCUMENTS 2801316 7/1979 Fed. Rep. of Germany .

Primary Examiner—Allen J. Robinson
Attorney, Agent, or Firm—Frederick H. Rabin

[57] ABSTRACT

Novel halogen-substituted N-(3-trifluoromethyl-4-halogenoalkoxyphenyl)-N'-benzoylureas of the formula

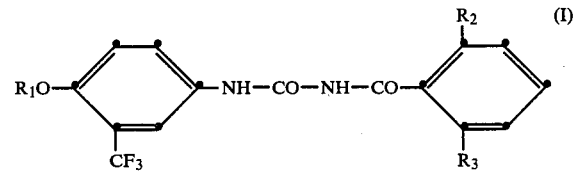

wherein $R_1$ is a $C_1$-$C_4$-alkyl group which is substituted at least twice by fluorine, chlorine or bromine, $R_2$ is fluorine or chlorine, and $R_3$ is hydrogen, fluorine or chlorine; processes for producing these compounds, as well as compositions containing them, for use in combating pests, particularly for combating insects which infest plants and animals. The novel compounds are especially effective against larval stages of insects which damage plants by eating.

8 Claims, No Drawings

INSECTICIDAL PHENYLUREAS AND METHODS OF USE THEREOF

The present invention relates to novel halogen-substituted N-(3-trifluoromethyl-4-halogenoalkoxy-phenyl)-N'-benzoylureas, to processes for producing them, and to their use in combating pests.

The halogen-substituted N-(3-trifluoromethyl-4-halogenoalkoxy-phenyl)-N'-benzoylureas according to the invention have the formula I

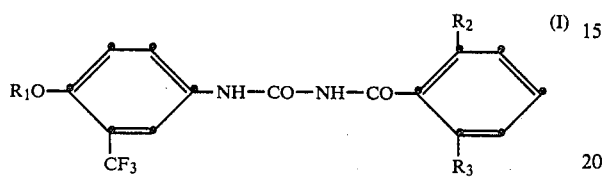

wherein $R_1$ is a $C_1$–$C_4$-alkyl group which is substituted at least twice by fluorine, chlorine or bromine, $R_2$ is fluorine or chlorine, and $R_3$ is hydrogen, fluorine or chlorine.

Compounds of the formula I according to the invention preferred by virtue of their action as pesticidal substances are those wherein $R_1$ is the —$CF_2$—$CHX_1X_2$ group, in which $X_1$ is fluorine, chlorine or bromine, preferably fluorine, and $X_2$ is fluorine, chlorine, bromine or trifluoromethyl. Particularly important compounds of the formula I are those wherein $R_1$ is the —$CF_2$—$CHF$—$CF_3$ group.

To be emphasised are also compounds of the formula I wherein $R_2$ and $R_3$ are each fluorine, or $R_2$ and $R_3$ are each chlorine, and also those compounds wherein $R_2$ is fluorine or chlorine, and $R_3$ is hydrogen.

The compounds of the formula I can be produced by processes known per se (cp. inter alia German Offenlegungsschriften Nos. 2,123,236 and 2,601,780).

Thus, for example, a compound of the formula I can be obtained by reaction (a) of a compound of the formula II

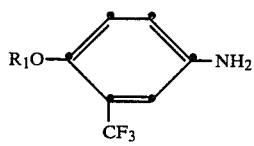

with a compound of the formula III

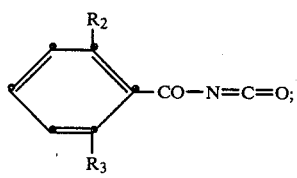

or (b) of a compound of the formula IV

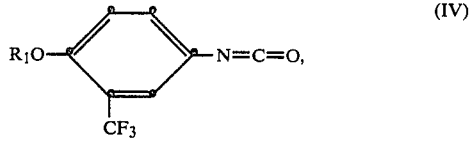

optionally in the presence of an organic or inorganic base, with a compound of the formula V $$\underset{R_3}{\underset{|}{\overset{R_2}{\overset{|}{\bigcirc}}}}-CO-NH_2. \quad (V)$$

In the above formulae II, III, IV and V, the symbols $R_1$, $R_2$ and $R_3$ have the meanings defined under the formula I.

The mentioned processes (a) and (b) are preferably performed under normal pressure, and in the presence of an inert organic solvent or diluent. Suitable solvents or diluents are for example: ethers and ethereal compounds, such as diethyl ether, dipropyl ether, dibutyl ether, dioxane, dimethoxyethane and tetrahydrofuran; N,N-dialkylated carboxylic acid amides; aliphatic, aromatic as well as halogenated hydrocarbons, especially benzene, toluene, xylene, chloroform, methylene chloride, carbon tetrachloride and chlorobenzene; nitriles, such as acetonitrile or propionitrile; dimethyl sulfoxide, as well as ketones, for example methyl ethyl ketone, methyl isopropyl ketone and methyl isobutyl ketone. Process (a) is generally performed at a temperature of −10° to 100° C., preferably between 0° and 25° C., optionally in the presence of an organic base, for example triethylamine. Process (b) is performed at a temperature of 0° to 150° C., preferably at the boiling point of the employed solvent, and optionally in the presence of an organic base, such as pyridine, or with the addition of an alkali metal or alkaline-earth metal, preferably sodium.

The starting materials of the formulae II, III, IV and V are known, or they can be produced by processes analogous to known processes. Thus, the substituted anilines of the formula II can be produced, according to processes known from the literature, by for example reducing with hydrogen 2-trifluoromethyl-4-nitrophenol (cp. J. Org. Chem. 27 (1962), 4660) in the presence of acetic anhydride, and etherifying the formed 2-trifluoromethyl-4-acetaminophenol with appropriate halogen-substituted alkenes, in a manner analogous to that described in Am. Soc. 73 (1951), 5831. The N-acetyl group is subsequently split off in the customary manner to obtain the anilines of the formula II. Some of these anilines are moreover obtainable using a process analogous to that shown in J. Org. Chem. 29 (1964), 1 (cp. also the literature cited therein).

One method group others for obtaining the benzoylisocyanates of the formula III is as follows (cp. J. Agr. Food Chem. 21, pp. 348 and 993, 1973):

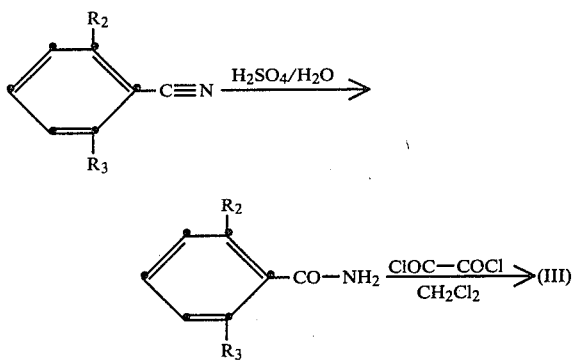

The substituted phenylisocyanates of the formula IV can be produced for example by reacting the appropriate anilines of the formula II with phosgene, using in general customary processes. The benzamides of the formula V to be used as starting materials are in most cases known (cp. Beilstein "Handbuch der organischen Chemie" Vol. 9, p. 336).

It is already known that specific N-phenyl-N'-benzoylureas have insecticidal properties (cp. German Offenlegungsschriften Nos. 2,123,236, 2,504,982 and 2,537,413, the Belgian Patent Nos. 832,304, 843,906 and 844,066, and also the U.S. Patent Specifications Nos. 4,085,226 and 4,089,975). Furthermore, in the German Offenlegungsschriften Nos. 2,601,780, 2,726,684 and 2,820,696 are described insecticidally effective halogen-substituted N-halogenoalkoxyphenyl-N'-benzoylureas.

It has now been found that surprisingly the N-(3-trifluoromethyl-4-halogenoalkoxy-phenyl)-N'-benzoylureas of the formula I according to the invention, whilst having high tolerance to plants and negligible toxicity to warmblooded animals, exhibit against pests which infest plants and animals, particularly against insect larvae, a degree of effectiveness greater than that of the aforementioned compounds known from the prior art.

The compounds of the formula I are especially suitable for combating insects of the orders: Lepidoptera, coleoptera, Homoptera, Heteroptera, Diptera, Thysanoptera, Orthoptera, Anoplura, Siphonaptera, Mallophaga, Thysanura, Isoptera, Psocoptera and Hymenoptera.

The compounds of the formula I are suitable in particular for combating insects which damage plants by eating, in crops of ornamental plants and productive plants, especially in cotton crops (for example against *Spodoptera littoralis* and *Heliothis virescens*), and also in vegetable crops (for example against *Leptinotarsa decemlineata*). The compounds of the formula I are characterised by a marked activity against larval insect stages, particularly against larval stages of insects which do damage by eating. When compounds of the formula I are taken with the feed by adult insect stages, there is observed in many cases, especially with Coleoptera, for example Anthonomus grandis, a reduced oviposition and/or a lessened hatching rate.

The compounds of the formula I are moreover suitable for combating ectoparasites, such as *Lucilia sericata*, in domestic animals and in productive animals, for example by treatment of animals, livestock housing and pasture land.

The action of the compounds according to the invention or of compositions containing them can be considerably broadened and adapted to suit prevailing conditions by the addition of other insecticides and/or acaricides. Suitable additives are for example the following active substances: organic phosphorus compounds, nitrophenols and derivatives thereof, formamidines, ureas, carbamates, pyrethroids and chlorinated hydrocarbons.

The compounds of the formula I can be combined with particular advantage also with substances which intensify pesticidal activity. Examples of compounds of this type are, inter alia: piperonylbutoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The compounds of the formula I can be used on their own or together with suitable carriers and/or additives. Suitable carriers and additives may be solid or liquid and correspond to the substances common in formulation practice, such as natural or regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays, solutions or suspensions, the formulation of these preparations being effected in a manner commonly known in the art. Also to be mentioned are cattle dips and spray races, in which aqueous preparations are used. These forms of preparation are particularly suitable for combating zooparasitic pests.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

solid preparations: dusts, scattering agents or granulates (coated granules, impregnated granules and homogeneous granules);

liquid preparations:
  (a) water-dispersible concentrates of active substance: wettable powders, pastes and emulsions; and
  (b) solutions.

The content of active substance in the described compositions is between 0.1 and 95%.

The active substances of the formula I can be formulated for example as follows:

Dusts

The following substances are used to produce (a) a 5% dust and (b) a 2% dust:

(a)
  5 parts of active substance,
  95 parts of talcum; and (b)
  2 parts of active substance,
  1 part of highly dispersed silicic acid, and
  97 parts of talcum.

The active substance is mixed and ground with the carriers.

Granulate

The following ingredients are used to produce a 5% granulate;
5 parts of active substance, 0.25 part of epoxidised vegetable oil,
0.25 part of cetyl polyglycol ether,
3.50 parts of polyethylene glycol, and
91 parts of kaolin (particle size 0.3-0.8 mm).

The active substance is mixed with epoxidised vegetable oil and dissolved in 6 parts of acetone, and the polyethylene glycol and cetyl polyglycol ether are then added. The solution obtained is sprayed onto kaolin and the acetone is subsequently evaporated off in vacuo.

Wettable powders

The following constituents are used to produce (a) a 40% wettable power, (b) and (c) a 25% wettable powder, and (d) a 10% wettable powder:
(a)
  40 parts of active substance,
  5 parts of sodium lignin sulfonate,
  1 part of sodium dibutyl-naphthalene sulfonate, and
  54 parts of silicic acid;
(b)
  25 parts of active substance,
  4.5 parts of calcium lignin sulfonate,
  1.9 parts of Champagne chalk/hydroxyethyl cellulose mixture (1:1),
  1.5 parts of sodium dibutyl-naphthalene sulfonate,
  19.5 parts of silicic acid,
  19.5 parts of Champagne chalk, and
  28.1 parts of kaolin;
(c)
  25 parts of active substance,
  2.5 parts of isooctylphenoxy-polyoxyethyleneethanol,
  1.7 parts of Champagne chalk/hydroxyethyl cellulose mixture (1:1),
  8.3 parts of sodium aluminium silicate,
  16.5 parts of kieselgur, and
  46 parts of kaolin; and
(d)
  10 parts of active substance,
  3 parts of a mixture of the sodium salts of saturated fatty alcohol sulfates,
  5 parts of naphthalenesulfonic acid/formaldehyde condensate, and
  82 parts of kaolin.

The active substance is intimately mixed in suitable mixers with the additives, and the mixture is then ground in the appropriate mills and rollers to obtain wettable powders which can be diluted with water to give suspensions of the desired concentration.

Emulsifiable concentrates

The following substances are used to produce (a) a 10% emulsifiable concentrate, (b) a 25% emulsifiable concentrate and (c) a 50% emulsifiable concentrate:
(a)
  10 parts of active substance,
  3.4 parts of epoxidised vegetable oil,
  3.4 parts of a combination emulsifier consisting of fatty alcohol polyglycol ether and alkylaralkyl-sulfonate calcium salt,
  40 parts of dimethylformamide, and
  43.2 parts of xylene;
(b)
  25 parts of active substance,
  2.5 parts of epoxidised vegetable oil,
  10 parts of an alkylarylsulfonate/fatty alcohol polyglycol ether mixture,
  5 parts of dimethylformamide, and
  57.5 parts of xylene; and
(c)
  50 parts of active substance,
  4.2 parts of tributylphenol-polyglycol ether,
  5.8 parts of calcium-dodecylbenzenesulfonate,
  20 parts of cyclohexanone, and
  20 parts of xylene.

Emulsions of the concentration required can be prepared from these concentrates by dilution with water.

Spray

The following constituents are used to produce (a) a 5% spray and (b) a 95% spray:
(a)
  5 parts of active substance,
  1 part of epoxidised vegetable oil,
  94 parts of ligroin (boiling limits 160°-190° C.);
(b)
  95 parts of active substance, and
  5 parts of epoxidised vegetable oil.

Example 1

5.4 g of 3-trifluoromethyl-4-(1,1,2,2-tetrafluoroethoxy)-aniline are placed into 20 ml of abs. ether, and 3.7 g of 2,6-difluorobenzoylisocyanate dissolved in 10 ml of abs. ether are subsequently added dropwise at room temperature. The solid which has precipitated is filtered off with suction after 1 hour; it is then washed with abs. ether and dried in air. Recrystallisation from toluene yields N-[3-trifluoromethyl-4-(1,1,2,2-tetrafluoroethoxy)-phenyl]-N'-(2,6-difluorobenzoyl)-urea having a melting point of 182°-185° C.

The following compounds of the formula I are produced in a manner analogous to that described above:

| $R_1$ | $R_2$ | $R_3$ | Melting point [°C.] |
|---|---|---|---|
| —$CF_2$—$CHF_2$ | F | F | 182-185 |
| —$CF_2$—$CHF_2$ | Cl | H | 156-157 |
| —$CF_2$—$CHF_2$ | F | Cl | 146-147 |
| —$CF_2$—CHFBr | F | F | 187 |
| —$CF_2$—CHFBr | F | Cl | 137-141 |
| —$CF_2$—CHFCl | F | F | 189-192 |
| —$CF_2$—CHFCl | F | Cl | 152-154 |
| —$CF_2$—$CHF_2$ | Cl | Cl | 167-169,5 |
| —$CHF_2$ | F | F | 167-169 |
| —$CHF_2$ | Cl | Cl | 231-233 |
| —$CHF_2$ | Cl | H | 170-172 |
| —$CF_3$ | Cl | Cl | |
| —$CF_3$ | F | F | |
| —$CF_3$ | Cl | F | |
| —$CF_3$ | F | H | |
| —$CHCl_2$ | F | F | |
| —$CF_2$—CHFCL | Cl | Cl | 155,5-156,5 |
| —$CF_2$—CHFBr | Cl | Cl | 146-150 |
| —$CF_2$—CHFCl | Cl | H | 163-165 |
| —$CF_2$—CHFBr | Cl | H | 153-155 |
| —$CF_2$—CHFBr | F | H | 135-136 |
| —$CF_2$—$CHCl_2$ | Cl | H | 153-154 |
| —$CF_2$—$CHCl_2$ | F | F | 186-191 |
| —$CF_2$—CHF—$CF_3$ | F | F | 185-187 |
| —$CF_2$—$CHF_2$ | F | H | 148-150 |
| —$CF_2$—CHFCl | F | H | 148-149 |
| —$CF_2$—CHFBr | F | H | |
| —$CF_2$—$CHCl_2$ | Cl | Cl | 154-157 |
| —$CF_2$—$CHCl_2$ | F | Cl | 165-167 |
| —$CF_2$—$CHCl_2$ | F | H | 148-150 |
| —$CF_2$—CHF—$CF_3$ | F | Cl | 149-151 |
| —$CF_2$—CHF—$CF_3$ | Cl | Cl | 154-158 |
| —$CF_2$—CHF—$CF_3$ | Cl | H | 136-138 |
| —$CF_2$—CHF—$CF_3$ | F | H | 120-122 |
| —CF($CF_3$)—CHF—$CF_3$ | F | F | |
| —CF($CF_3$)—CHF—$CF_3$ | F | H | |

-continued

| $R_1$ | $R_2$ | $R_3$ | Melting point [°C.] |
|---|---|---|---|
| —CF(CF$_3$)—CHF—CF$_3$ | Cl | Cl | |

EXAMPLE 2

Action against *Musca domestica*

50 g of freshly prepared CSMA nutrient medium for maggots were weighed off into each of a series of beakers. A specific amount of a 1% (by weight) acetonic solution of the respective active substance was transferred by pipette to the nutrient medium in each beaker. After a thorough mixing of the nutrient medium, the acetone was allowed to evaporate off for at least 20 hours. There were then deposited per active substance and concentration in each case 25 one-day-old Musca domestica maggots into each beaker containing the treated nutrient medium. After completion of pupation, the formed pupae were separated from the nutrient medium by flushing with water, and were placed into vessels closed with perforated lids. The pupae flushed out per batch were counted (toxic effect of the active substance on the development of the maggot), and after 10 days the number of flies which had emerged from the pupae was determined.

Compounds according to Example 1 exhibited a good action in the above test.

EXAMPLE 3

Action against *Lucilia sericata*

1 ml of an aqueous solution containing 0.5% of active substance was placed onto 9 ml of a culture medium at 50° C. About 30 freshly hatched Lucilia sericata larvae were then settled onto the culture medium, and after 48 and 96 hours, respectively, the insecticidal action was determined on the basis of the mortality rate which had resulted.

Compounds according to Example 1 exhibited in this test a good action against Lucilia sericata.

EXAMPLE 4

Action against *Aëdes aegypti*

Sufficient of a 0.1% acetonic solution of the respective active substance was transferred by pipette to the surface of 150 ml of water in a container to obtain concentrations of 10, 5 and 1 ppm in each case. After the acetone had evaporated off, 30–40 two-day-old Aëdes larvae were placed into each container. The mortality rate was ascertained after 1, 2 and 5 days, respectively.

Compounds according to Example 1 exhibited in this test a good action against *Aedes aegypti*

EXAMPLE 5

Insecticidal action against eating insects

Cotton plants were sprayed with a 0.05% aqueous active-substance emulsion (obtained from a 10% emulsifiable concentrate). After the drying of the applied coating, larvae of Spodoptera littoralis in the L$_3$-stage and of *Heliothis virescens* in the L$_3$-stage, respectively, were settled onto the cotton plants. The test was carried out at 28° C. with 60% relative humidity. At intervals in each case of 24 hours, an assessment was made of the mortality rate and also of development and shedding disturbances suffered by the deposited larvae.

Compounds according to Example 1 exhibited in the above test a good insecticidal action against larvae of Spodoptera littoralis and Heliothis virescens.

EXAMPLE 6

Action against *Epilachna varivestis* (larvae)

*Phaseolus vulgaris* plants (bush beans) about 15–20 cm in height were sprayed with an aqueous emulsion preparation containing the active substance to be tested. After the drying of the applied coating, 10 larvae of Epilachna varivestis (Mexican bean beetle) in the 4th larval stage were settled onto each plant. A plastics cylinder covered with a copper-gauze lid was placed over the treated plants. After 1 and 2 days, respectively, the acute action (% mortality) was determined. The test insects were observed for a further 3 days to effect an evaluation with respect to any damage on the plants from eating (antifeeding effect), and disturbances in development and in shedding.

Compounds according to Example 1 exhibited a good action in the above test.

EXAMPLE 7

Action against *Leptinotarsa decemlineata* (larvae)

15 cm tall potato plants in culture vessels were evenly sprayed until dripping wet, using a compressed-air sprayer, with an aqueous emulsion preparation containing the active substance to be tested at a concentration of 500 ppm. After the drying of the coating on the plants, that is to say, after about one and a half hours, a plastics cylinder was placed over the plants, and onto each plant were settled 10 Colorado beetle larvae of the 3rd stage. The cylinders were then closed with a copper-gauze lid, and the specimens were left in darkness at 28° C. with 60% relative humidity. After 1 and 2 hours, and also after 1, 2 and 8 days, respectively, an examination was made to determine the mortality rate of the test insects (dorsal position) and the percentage damage caused by eating on the plants.

Compounds according to Example 1 exhibited a good action in the above test.

EXAMPLE 8

Chemosterilising action against *Anthonomus grandis*

Adult *Anthonomus grandis*, which had been hatched no longer than 24 hours, were transferred, in groups each of 25 beetles, to cages having lattice walls. The cages containing the beetles were then immersed for 5 to 10 seconds in an acetonic solution containing 1.0 percent by weight of the active substance to be tested. After the beetles were again dry, they were placed, for copulation and oviposition, into covered dishes containing feed. Deposited eggs were flushed out with running water two to three times weekly; they were counted, disinfected by being placed for two to three hours in an aqueous disinfectant (such as "Actamer B 100"), and then deposited into dishes containing a suitable larval diet. The eggs were examined after 7 days to determine whether larvae had developed from the deposited eggs.

In order to ascertain the duration of the chemosterilant effect of the active substances tested, the oviposition of the beetles was observed during a period of about four weeks. The evaluation was on the basis of the reduction of the number of eggs laid and hatched larvae in comparison with that of untreated control specimens. Compounds according to Example 1 exhibited high activity in this test.

What is claimed is:

1. A compound of the formula I

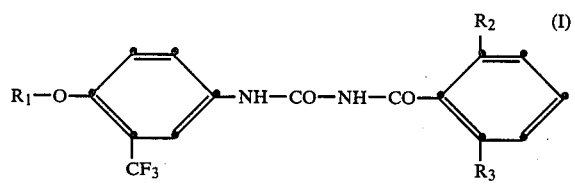

wherein $R_1$ is the $-CF_2-CHF-CF_3$ group, $R_2$ is fluorine or chlorine, and $R_3$ is hydrogen, fluorine or chlorine.

2. A compound according to claim 1, wherein $R_2$ and $R_3$ are fluorine, or $R_2$ and $R_3$ are chlorine, or $R_2$ is fluorine or chlorine and $R_3$ is hydrogen.

3. A compound according to claim 1 of the formula

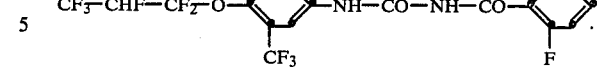

4. A compound according to claim 1 of the formula

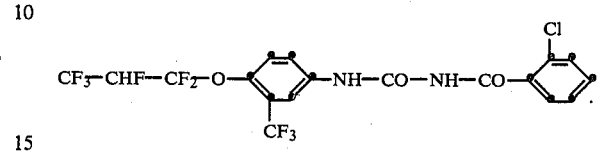

5. A compound according to claim 1 of the formula

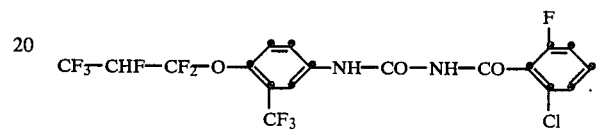

6. An insecticidal composition comprising an insecticidally effective amount of a compound according to claim 1 and a suitable carrier.

7. A method for combatting insects which comprises applying to said insects or to a locus desired to be protected from said insects an insecticidally effective amount of a compound according to claim 1.

8. A method according to claim 7, for combatting larvae stages of insects which damage plants.

* * * * *